United States Patent
Hongo et al.

(10) Patent No.: US 9,316,576 B2
(45) Date of Patent: Apr. 19, 2016

(54) SAMPLE DETECTION APPARATUS AND DETECTION METHOD

(71) Applicant: KABUSHIKI KAISHA TOSHIBA, Minato-ku, Tokyo (JP)

(72) Inventors: Sadato Hongo, Yokohama (JP); Kentaro Kobayashi, Tokyo (JP); Hideto Furuyama, Yokohama (JP)

(73) Assignee: KABUSHIKI KAISHA TOSHIBA, Tokyo (JP)

( * ) Notice: Subject to any disclaimer, the term of this patent is extended or adjusted under 35 U.S.C. 154(b) by 107 days.

(21) Appl. No.: 14/011,666

(22) Filed: Aug. 27, 2013

(65) Prior Publication Data
US 2014/0255911 A1  Sep. 11, 2014

(30) Foreign Application Priority Data

Mar. 7, 2013  (JP) ................. 2013-045394

(51) Int. Cl.
*G01N 15/12* (2006.01)
*G01N 33/53* (2006.01)
*G01N 33/543* (2006.01)
(Continued)

(52) U.S. Cl.
CPC ............ *G01N 15/12* (2013.01); *G01N 15/1031* (2013.01); *G01N 33/53* (2013.01); *G01N 33/5438* (2013.01); *G01N 33/587* (2013.01); *G01N 2015/1087* (2013.01); *G01N 2015/1093* (2013.01)

(58) Field of Classification Search
CPC . G01N 15/12; G01N 33/587; G01N 33/5438; G01N 15/1031; G01N 33/53
See application file for complete search history.

(56) References Cited

U.S. PATENT DOCUMENTS

| | | | |
|---|---|---|---|
| 7,297,151 B2 | 11/2007 | Boecker et al. | |
| 7,390,388 B2 | 6/2008 | Childers et al. | |
| 7,604,592 B2 | 10/2009 | Freeman et al. | |

(Continued)

FOREIGN PATENT DOCUMENTS

| | | | |
|---|---|---|---|
| JP | 2001088096 A | 4/2001 | |
| JP | 2003315349 A | 11/2003 | |

(Continued)

OTHER PUBLICATIONS

U.S. Appl. No. 14/011,640, First Named Inventor: Kentaro Kobayashi, Title: "Semiconductor Micro Analysis Chip and Sample Liquid Flowing Method", filed Aug. 27, 2013.

(Continued)

*Primary Examiner* — Melanie Y Brown
(74) *Attorney, Agent, or Firm* — Holtz, Holtz & Volek PC

(57) ABSTRACT

According to one embodiment, a sample detection apparatus including an insulating partition to divide a first and a second region, a pore formed in the partition, a first electrode arranged in the first region, a second electrode arranged in the second region, a power source configured to apply electrical current between the first and second electrode in a state in which a reagent containing a capture substance to be bound to a target and a tag particle bound to the capture substance is introduced into the first region together with a sample, and an electrolyte solution is introduced into the second region, a measurement unit configured to observe a change in a conductive state, and a detection unit to detect presence/absence of the target in the sample based on an observation result.

5 Claims, 9 Drawing Sheets

(51) Int. Cl.
 *G01N 33/58* (2006.01)
 *G01N 15/10* (2006.01)

(56) References Cited

U.S. PATENT DOCUMENTS

| | | |
|---|---|---|
| 7,883,665 B2 | 2/2011 | Aizenberg et al. |
| 7,977,122 B2 | 7/2011 | Sandoz et al. |
| 8,157,410 B2 | 4/2012 | Tang et al. |
| 8,182,635 B2 | 5/2012 | Ayliffe et al. |
| 8,409,523 B2 | 4/2013 | Mendel-Hartvig et al. |
| 8,608,891 B2 | 12/2013 | Ayliffe et al. |
| 8,722,423 B2 | 5/2014 | Bergman et al. |
| 8,759,115 B2 | 6/2014 | Ohman et al. |
| 8,821,812 B2 | 9/2014 | Ohman et al. |
| 8,974,749 B2 | 3/2015 | Bergman et al. |
| 2003/0040173 A1 | 2/2003 | Fonash et al. |
| 2003/0119034 A1 | 6/2003 | Kang et al. |
| 2004/0144658 A1 | 7/2004 | Flory |
| 2005/0019784 A1* | 1/2005 | Su et al. ............... 435/6 |
| 2005/0042766 A1 | 2/2005 | Ohman et al. |
| 2006/0035386 A1 | 2/2006 | Hattori et al. |
| 2006/0073489 A1* | 4/2006 | Li et al. ............... 435/6 |
| 2007/0242560 A1 | 10/2007 | Norikane et al. |
| 2008/0278728 A1 | 11/2008 | Tetz et al. |
| 2008/0311375 A1 | 12/2008 | Harnack et al. |
| 2009/0136958 A1 | 5/2009 | Gershow et al. |
| 2009/0194429 A1* | 8/2009 | Hibbs et al. ............... 205/778 |
| 2009/0208920 A1 | 8/2009 | Öhman et al. |
| 2011/0291026 A1 | 12/2011 | Renna et al. |
| 2012/0043202 A1 | 2/2012 | Miyamura et al. |
| 2012/0115130 A1* | 5/2012 | Imai ............... G01N 33/5047 435/6.1 |
| 2012/0142904 A1* | 6/2012 | He ............... B01D 57/02 530/412 |
| 2012/0228730 A1 | 9/2012 | Akiyama et al. |
| 2012/0258479 A1 | 10/2012 | Ding et al. |
| 2012/0292496 A1 | 11/2012 | Escobedo et al. |
| 2013/0065777 A1 | 3/2013 | Altug et al. |
| 2014/0158540 A1 | 6/2014 | Ohura |

FOREIGN PATENT DOCUMENTS

| | | |
|---|---|---|
| JP | 2004219370 A | 8/2004 |
| JP | 2004317340 A | 11/2004 |
| JP | 2004325304 A | 11/2004 |
| JP | 2004354364 A | 12/2004 |
| JP | 2005098818 A | 4/2005 |
| JP | 2005230647 A | 9/2005 |
| JP | 2005532151 A | 10/2005 |
| JP | 2006090910 A | 4/2006 |
| JP | 2006-130400 A | 5/2006 |
| JP | 2007-090135 A | 4/2007 |
| JP | 2007170840 A | 7/2007 |
| JP | 2008039541 A | 2/2008 |
| JP | 4366327 B2 | 11/2009 |
| JP | 2009264904 A | 11/2009 |
| JP | 2009541737 A | 11/2009 |
| JP | 2010185703 A | 8/2010 |
| JP | 2010187664 A | 9/2010 |
| JP | 2012255810 A | 12/2012 |
| JP | 2013036865 A | 2/2013 |
| JP | 2014521956 A | 8/2014 |
| WO | 2009126257 A1 | 10/2009 |
| WO | 2013016486 A1 | 1/2013 |
| WO | WO 2013/137209 A1 | 9/2013 |

OTHER PUBLICATIONS

U.S. Appl. No. 14/012,566, First Named Inventor: Kentaro Kobayashi, Title: "Semiconductor Micro Analysis Chip and Manufacturing Method Thereof", filed Aug. 28, 2013.

U.S. Appl. No. 14/012,599, First Named Inventor: Kentaro Kobayashi, Title: "Semiconductor Analysis Microchip and Method of Manufacturing the Same", filed Aug. 28, 2013.

U.S. Appl. No. 14/198,425, First Named Inventor: Hiroko Miki, Title: "Semiconductor Micro-Analysis Chip and Method of Manufacturing the Same", filed Mar. 5, 2014.

Related U.S. Appl. No. 14/484,305; First Named Inventor: Sadato Hongo; Title: "Single Particle Analyzer and Single Particle Analysis Method"; filed Sep. 12, 2014.

Japanese Office Action (and English translation thereof) dated Aug. 4, 2015, issued in counterpart Japanese Application No. 2013-045394.

* cited by examiner

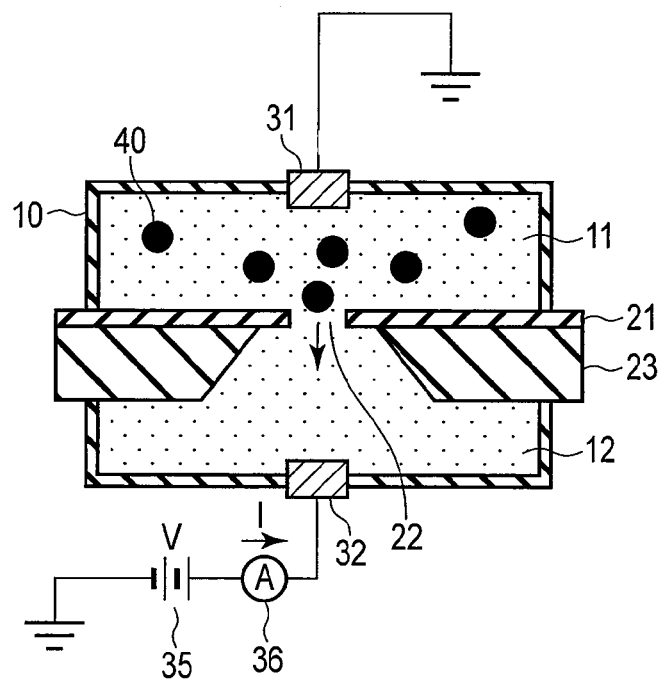
F I G. 1
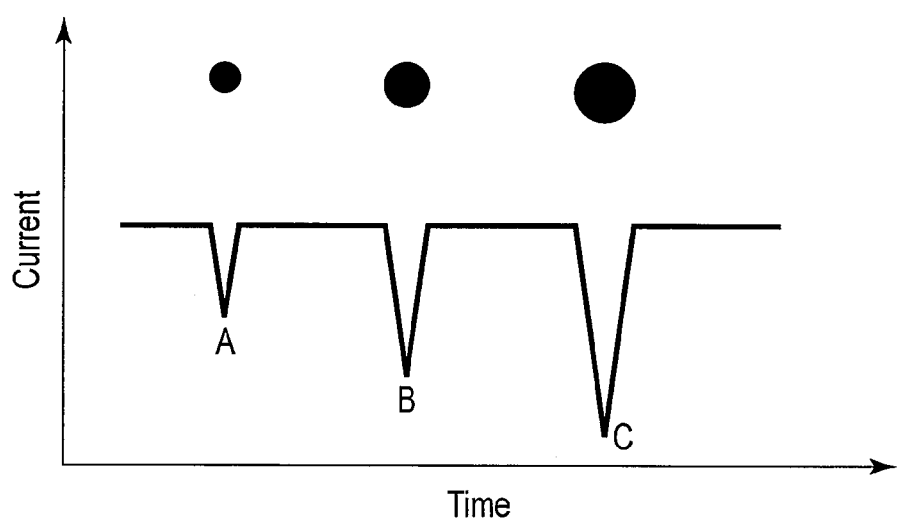
F I G. 2

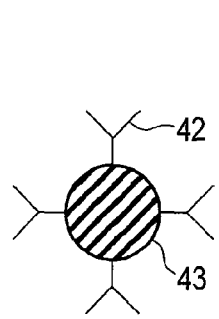
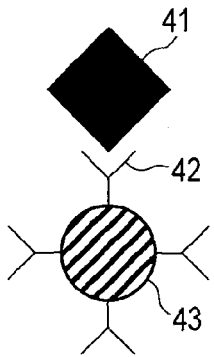
FIG. 3A  FIG. 3B
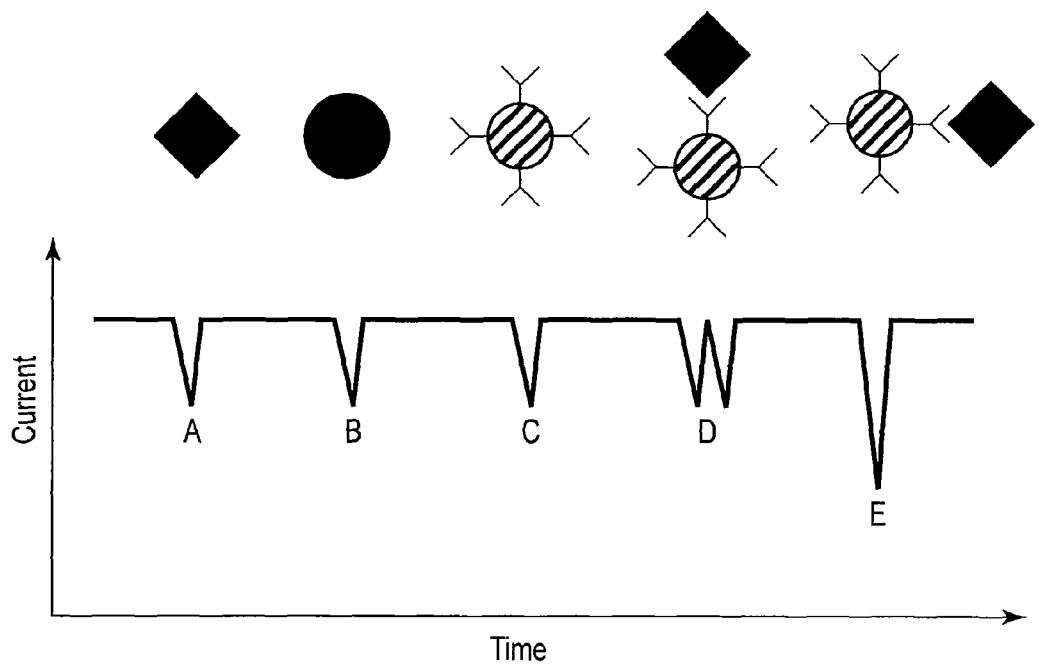
FIG. 4

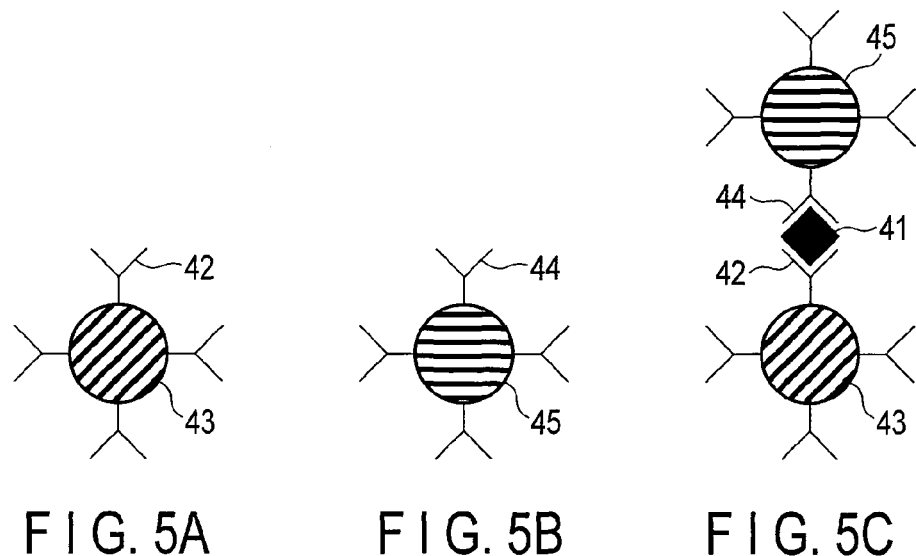
F I G. 5A    F I G. 5B    F I G. 5C
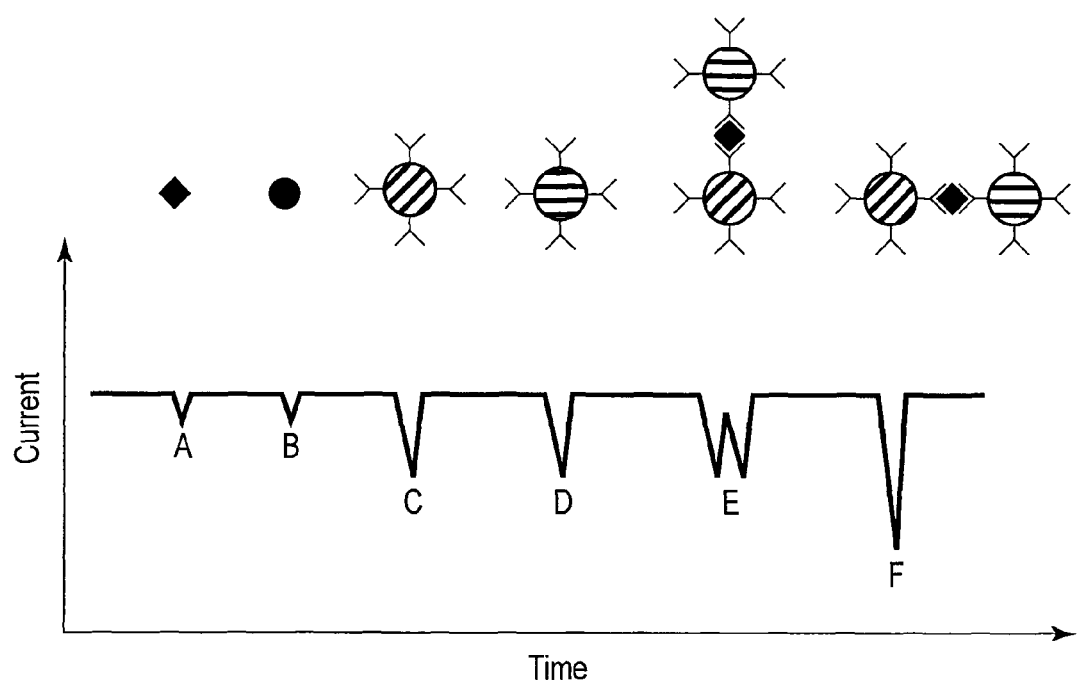
F I G. 6

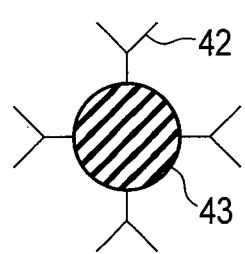
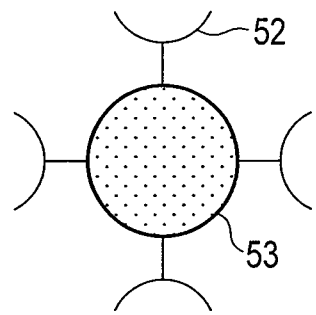
FIG. 7A      FIG. 7B
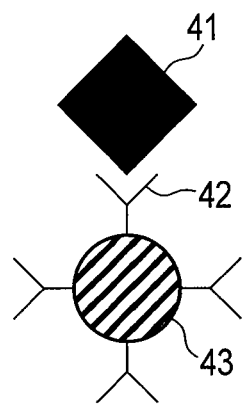
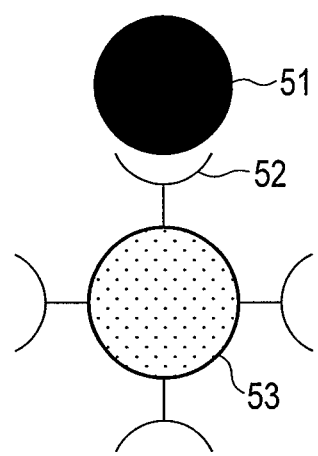
FIG. 7C      FIG. 7D

SAMPLE DETECTION APPARATUS AND DETECTION METHOD

CROSS-REFERENCE TO RELATED APPLICATIONS

This application is based upon and claims the benefit of priority from Japanese Patent Application No. 2013-045394, filed Mar. 7, 2013, the entire contents of which are incorporated herein by reference.

FIELD

Embodiments described herein relate generally to a sample detection apparatus and a detection method for detecting a virus, a bacterium, or the like.

BACKGROUND

For testing influenza viruses, a rapid test kit is recently used in hospitals and clinics to detect a virus or determine the A/B type using gold colloid particles modified by antibodies. However, the currently used rapid test kit has only a high minimum detection limit. This poses a problem of so-called window period, leading to a failure in obtaining a positive test result in several hours after infection because the multiplication of influenza viruses in the body is still insufficient.

Note that genetic screening can solve the problem of undetected errors caused by the shortage in the minimum detection sensitivity. However, the genetic screening is expensive and time-consuming. There exist apparatuses for detecting the shapes or sizes of fine particles passing through a pore on a one-by-one basis. However, it is impossible to determine viruses having an equal shape or size. Hence, there is presently no apparatus capable of easily detecting a virus or a bacterium in a short time at a high sensitivity.

BRIEF DESCRIPTION OF THE DRAWINGS

FIG. 1 is a sectional view showing the schematic arrangement of a detection unit used in a biomolecule detection apparatus according to the first embodiment;

FIG. 2 is a timing chart showing a current signal that changes depending on the grain size;

FIGS. 3A and 3B are views showing an example of a reagent used in the first embodiment;

FIG. 4 is a timing chart showing a current signal detected in the first embodiment;

FIGS. 5A to 5C are views showing an example of a reagent used in the second embodiment;

FIG. 6 is a timing chart showing a current signal detected in the second embodiment;

FIGS. 7A to 7D are views showing an example of a reagent used in the third embodiment;

DETAILED DESCRIPTION

Figure 8:
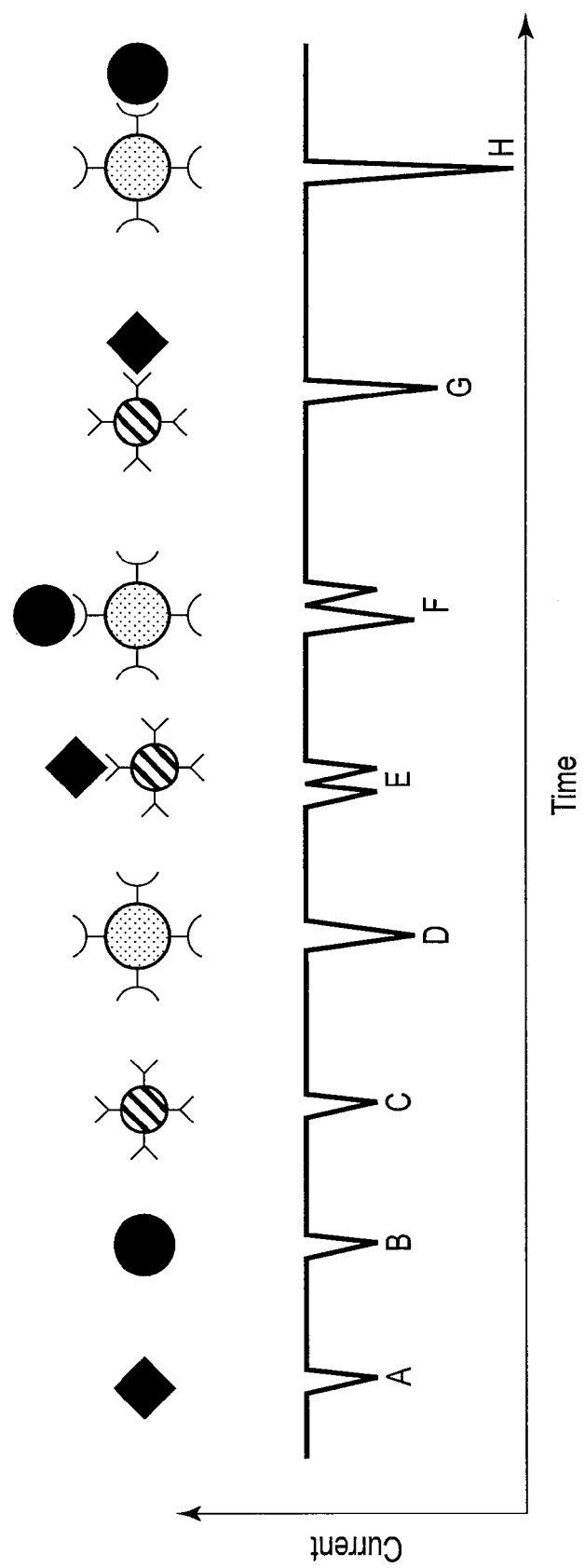
FIG. 8 is a timing chart showing a current signal detected in the third embodiment.

In general, according to one embodiment, a sample detection apparatus comprising: an insulating partition configured to divide a first region and a second region; a pore formed in the partition and configured to make the first chamber and the second region communicate; a first electrode arranged in the first region; a second electrode arranged in the second region; a power source configured to apply electrical current between the first electrode and the second electrode through the pore in a state in which a reagent containing a capture substance to be specifically bound to a target and a tag particle bound to the capture substance is introduced into the first region together with a sample, and an electrolyte solution is introduced into the second region; a measurement unit configured to observe a change in a conductive state between the first electrode and the second electrode when the target to be detected in the first region passes through the pore; and a detection unit configured to detect presence/absence of the target to be detected in the sample based on an observation result of the observation unit.

A sample detection apparatus and a detection method according to each embodiment will now be described with reference to the accompanying drawing.

(First Embodiment)
(Arrangement of Detection Unit)

FIG. 1 is a sectional view showing the schematic arrangement of a detection unit used in a biomolecule detection apparatus according to the first embodiment.

As shown in FIG. 1, the detection unit in the biomolecule detection apparatus includes a measurement vessel 10 that can be filled with a liquid. The vessel 10 is divided into a first chamber (first region) 11 and a second chamber (second region) 12 by an insulating partition 21. A pore 22 is formed in the partition 21 so as to make the first chamber 11 and the second chamber 12 communicate with each other. The diameter of the pore 22 is slightly larger than that of a particle as a detection target. The partition 21 is supported by a substrate 23 having a sufficient thickness except the peripheral portion of the pore 22.

A first electrode 31 and a second electrode 32 are equipped on the walls of the vessel 10. The first electrode 31 is located so as to be partially exposed to the inside of the first chamber 11. The second electrode 32 is located so as to be partially exposed to the inside of the second chamber 12. A DC power supply 35 and a measurement circuit 36 are connected in series between the first electrode 31 and the second electrode 32.

The vessel 10 is composed of an electrically and chemically inactive material for the whole structure or the inner wall of the first chamber 11, the inner wall of the second chamber 12, the contact portion to the first electrode 31, and the contact portion to the second electrode 32. The vessel 10 is made of, for example, plastic, glass, sapphire, ceramic, resin, rubber, elastomer, $SiO_2$, $SiN$, $Al_2O_3$, or the like.

The partition 21 is composed of an electrically and chemically inactive insulating material. The partition 21 is made of, for example, film, plastic, glass, sapphire, ceramic, resin, rubber, elastomer, $SiO_2$, $SiN$, $Al_2O_3$, or the like.

(Measurement Method)

A method of measuring the size and shape of a particle using the apparatus shown in FIG. 1 will be described below.

The first chamber 11 and the second chamber 12 are filled with an electrolyte solution. At this time, a fluid channel is formed between the first chamber 11 and the second chamber 12 through the pore 22. The first chamber 11 includes targets (biomolecules) to be detected that are measurement targets and a reagent to be described later. Part of the first electrode 31 is inserted in the first chamber 11 and dipped in the liquid. Part of the second electrode 32 is inserted in the second chamber 12 and dipped in the liquid.

The liquid included in the first chamber 11 and the second chamber 12 need only be a liquid capable of conducting electrical current between the first electrode 31 and the second electrode 32. As the electrolyte solution, a KCl or NaCl solution or a buffer solution such as a buffer solution of tri ethylene diamine tetra acetic acid (TE) or phosphate-buffered saline (PBS) is usable.

In the state in which the first chamber 11 and the second chamber 12 are filled with the electrolyte solution, the DC power supply 35 apply voltage between the first electrode 31 and the second electrode 32. The measurement circuit 36 measures a current between the first electrode 31 and the second electrode 32. At this time, a target 40 to be detected in the first chamber 11 passes through the pore 22 and moves to the second chamber 12 in accordance with the electric field.

The amount of the current change when the target 40 to be detected passes through the pore 22 depends on the size and properties of the target 40 to be detected, as schematically shown in FIG. 2. In FIG. 2, when the target 40 to be detected is small, a small current change peak A is obtained. As the target 40 to be detected becomes large, the current change peak becomes large, as indicated by B and C. The change in the current which appears when the target 40 to be detected passes through the pore 22 depends on the properties of the target 40 to be detected. More specifically, when the target 40 to be detected functions to cut off the current flowing through the electrolyte solution, the current decreases. Conversely, when the target 40 to be detected facilitates the current flow, the current increases.

(Structure of Reagent and Detection Signal)

In this embodiment, assume that one type of detection targets (biomolecules) can exist in the sample. As shown in FIG. 3A, a capture substance 42 (for example, antibody) to be specifically bound to the detection target and a tag particle 43 bound to the capture substance 42 are used as a reagent. This reagent is introduced into the sample. If a detection target 41 exists in the sample, the tag particle 43 is bound to the detection target 41 via the capture substance 42, as shown in FIG. 3B. As the tag particle 43, for example, a negatively charged spherical polystyrene particle is usable.

The first chamber 11 is filled with the sample and the above-described reagent. At this time, the second chamber 12 is filled with the electrolyte solution. Note that the sample is a liquid capable of conducting current, and can include the target to be detected. When the sample is not an electrolyte solution, or when no sufficient liquid can be supplied to the first chamber 11 only by the sample, the sample is dissolved in an electrolyte solution and introduced into the first chamber 11.

In this state, a voltage is applied between the first electrode 31 and the second electrode 32 to conduct current. The particles in the first chamber 11 then move to the second chamber 12 through the pore 22. At this time, the current changes like a pulse.

The change in current depends on the size or shape of a passing particle, as shown in FIG. 4. More specifically, for the single detection target 41 (A), a single particle other than the detection target 41 (B), or the single tag particle 43 (C), a discrete detection signal, that is, a unimodal pulse signal according to the size of the fine particle is obtained.

On the other hand, when the detection target 41 and the tag particle 43 are bound via the capture substance 42 (D and E), the change in signal greatly differs from A to C. More specifically, when the detection target 41 and the tag particle 43 pass through the pore 22 in series, that is, sequentially time-serially (D), a current produced by the passage of the detection target 41 and a current produced by the passage of the tag particle 43 are continuously measured. That is, two continuous detection signals are obtained as a bimodal pulse signal. In contrast, when the detection target 41 and the tag particle 43 pass through the pore 22 in parallel, that is, parallel and side by side (E), a current produced by the passage of the detection target 41 and a current produced by the passage of the tag particle 43 are compositely measured. That is, the detection signal is obtained as a unimodal pulse signal having a large peak. When the detection target 41 and the tag particle 43 pass through the pore 22 in an intermediate state between D and E, that is, obliquely and side by side, an intermediate response signal between D and E is obtained, as a matter of course.

Hence, whether the detection target 41 is bound to the capture substance 42 can be determined by identifying the detection signal of the measurement circuit 36. In other words, if signals D and E shown in FIG. 4 are observed, it can be determined that the detection target 41 exists in a sample. Even for a biomolecule having the same size and shape as the detection target 41, it can be determined whether the biomolecule is of a type to be bound to the capture substance 42 or not.

The presence/absence of the detection target 41 can be measured by counting signals D and E shown in FIG. 4. To be more specific, an observation is made of a state where a change in the conductive state caused by passage of the detection target 41 and a change in the conductive state caused by passage of the tag particle 43 are continuous or occur in a composite manner. If such a state is observed more than a predetermined number of times, or if the distribution of the results obtained by observation performed by the predetermined number differs from observation distribution of the background particles, then it is determined that the detection target exists in the sample.

In addition, when signals D and E in FIG. 4 are counted by monitoring for a predetermined time, the density of the detection target can also be measured.

Note that the determination by the above-described method is possible when the detection target 41 and the tag particle 43 have an equal size. The size of the detection target 41 is realistically 100 nm or more, preferably 300 nm or more, and more preferably 500 nm or more. The tag particle 43 is preferably a particle having an equal size in accordance with the size of the detection target 41.

The apparatus shown in FIG. 1 can detect a signal produced by each particle passing through the pore 22. Hence, if at least one detection target 41 exists, it can be detected as a particle bound to the capture substance 42 capturing it and the tag particle 43.

As described above, according to this embodiment, the reagent containing the capture substance 42 bound to the detection target 41 and the tag particle 43 bound to the capture substance 42 is introduced together with the sample. The current change when the particle passes through the pore 22 is measured, thereby judging the presence/absence of the detection target 41 bound to the capture substance 42. It is therefore possible to detect/identify, among viruses or bacteria having an equal size or shape, a specific virus or bacterium in a short time at a high sensitivity using the specificity of the antigen-antibody reaction.

A simple case in which the capture substance 42 is bound to the detection target 41 only at one portion has been described above. However, the embodiment is not limited to this, and the same concept applies to a case in which the capture substance 42 is bound to the detection target 41 at a plurality of portions (epitopes). Note that when the capture substance 42 is bound at a plurality of portions, the tag particle and the detection target need not always have the same size. It is only necessary to identify the signal of another single particle, as in the above-described embodiment.

(Second Embodiment)

The arrangement of a biomolecule detection apparatus used in this embodiment is the same as in FIG. 1 described in the first embodiment.

In this embodiment, assume that one type of detection targets (biomolecules) can exist in a sample. Also assume that the particles are very small, and the current detection signal intensity for a single particle is small.

If only tag particles bound to a capture substance (antibody) to be specifically bound to the detection target are used as a reagent, as in the first embodiment, the size difference between the single tag particle and the bound state of the detection target and the tag particle is small because of the small size of the detection target. That is, it is difficult to obtain a clear difference in the current signal intensity by comparing the current detection signal intensity for the bound state of the detection target and the tag particle and that for the single tag particle.

A first tag particle 43 bound to a first capture substance 42 to be specifically bound to the first portion of a detection target 41, as shown in FIG. 5A, and a second tag particle 45 bound to a second capture substance 44 to be specifically bound to the second portion of the detection target 41, as shown in FIG. 5B, are used as a reagent. In this case, if the detection target 41 exists in the sample, the first tag particle 43 and the second tag particle 45 are bound to the detection target 41 via the first capture substance 42 and the second capture substance 44, as shown in FIG. 5C.

The size of the composite particle formed by binding the first tag particle 43 and the second tag particle 45 is much larger than that of the single first tag particle 43 or second tag particle 45. Hence, the current detection signal by the composite particle is greatly different from others. For this reason, observing the current detection signal by the composite particle formed by binding the first tag particle 43 and the second tag particle 45 gives proof of existence of the detection target 41.

That is, even when the size of the detection target 41 is very small, it can sufficiently be detected by causing the first tag particle 43 and the second tag particle 45 to have observable sizes. The sizes of the tag particles are 100 nm or more, preferably 300 nm or more, and more preferably 500 nm or more. The sizes of the first tag particle 43 and the second tag particle 45 can be either equal or different.

The same as described above can apply to a case in which the capture substances 42 and 44 are of the same type and are bound to different portions of the detection target. That is, if the form of the composite particle formed from the tag particles bound via the detection target is observed from the current signal, the existence of the detection target is shown. The same as described above can also apply to a case in which the capture substances 42 and 44 are of the same type and are bound to a plurality of different portions of the detection target. This makes it possible to detect even a very small particle such as a virus at a high sensitivity.

FIG. 6 schematically shows current detection signals in various states. The change in current depends on the size or shape of a passing particle, as in the first embodiment. More specifically, for the single detection target, the detection signal intensity is very low because the detection target is very small (A and B), and the detection target is rarely detected. On the other hand, for the single tag particle that is not bound to the detection target, the change in signal slightly increases, but the signal waveform indicates the simple single particle (C and D).

Conversely, when the first tag particle 43 and the second tag particle 45 are bound via the detection target 41 (E and F), the change in signal or the signal waveform is greatly different from A to D. More specifically, when the composite particle with the particles arranged in tandem passes through the pore 22, a continuous bimodal pulse signal (double-peak waveform) (E) is observed. When the composite particle with the particles arranged side by side passes through the pore 22, a large unimodal pulse signal (single peak signal) (F) is observed. When the particles pass through the pore 22 in an intermediate state between E and F, that is, obliquely side by side, an intermediate response signal between E and F is obtained, as in the first embodiment. In both cases, a signal different from A to D is obtained, and the existence of the detection target 41 can be determined.

The presence/absence of the detection target 41 can be measured by counting signals E and F shown in FIG. 6. To be more specific, an observation is made of a state where a change in the conductive state caused by passage of the pore 22 of the first tag particle 43 and a change in the conductive state caused by passage of the pore of the second tag particle 43 are continuous or occur in a composite manner. If such a state is observed more than a predetermined number of times, or if the distribution of the results obtained by observation performed by the predetermined number differs from observation distribution of the background particles, then it is determined that the detection target exists in the sample.

As described above, according to this embodiment, the first tag particle 43 bound to the first capture substance 42 to be specifically bound to the first portion of the detection target 41 and the second tag particle 45 bound to the second capture substance 44 to be specifically bound to the second portion of the detection target 41 are used as the reagent. This makes it possible to detect the detection target 41 that can exist in the sample even when the detection target is very small. Hence, it is possible to obtain the same effect as in the above-described first embodiment, as a matter of course, and also detect/identify, among viruses or bacteria having the same size or shape, a very small virus or bacterium at a high sensitivity using the specificity of the antigen-antibody reaction.

A case in which the tag particles are bound to the two, first and second portions of the detection target 41 via the capture substances has been described above for the sake of simplicity. However, the embodiment is not limited to this, and the same concept applies to a case in which the tag particles are bound to more portions. That is, if the form of the composite particle formed from the tag particles bound via the detection target is observed from the current signal, the existence of the detection target is revealed.

(Third Embodiment)

The arrangement of a biomolecule detection apparatus used in this embodiment is the same as in FIG. 1 described in the first embodiment.

In this embodiment, assume that two types of detection targets (biomolecules) can exist in a sample.

A first tag particle 43 bound to a first capture substance (first antibody) 42 to be specifically bound to a first detection target 41, as shown in FIG. 7A, and a second tag particle 53 bound to a second capture substance (second antibody) 52 to be specifically bound to a second detection target 51, as shown in FIG. 7B, are used as a reagent. The first tag particle 43 and the second tag particle 53 are made to have different sizes. When this reagent is introduced into the sample, the tag particle 43 is bound to the detection target 41 via the capture substance 42, as shown in FIG. 7C, and the tag particle 53 is bound to the detection target 51 via the capture substance 52, as shown in FIG. 7D.

A first chamber 11 is filled with the sample and the above-described reagent. A second chamber 12 is filled with an electrolyte solution. In this state, a voltage is applied between a first electrode 31 and a second electrode 32 to conduct current. The fine particles in the first chamber 11 then move to the second chamber 12 through a pore 22. At this time, the current changes like a pulse.

The change in current depends on the size or shape of a passing particle, as shown in FIG. 8. More specifically, for the single first detection target 41 (A), the single second detection target 51 (B), the single first tag particle 43 (C), and the single second tag particle 53 (D), a discrete detection signal according to the size of the fine particle is obtained.

On the other hand, when the first detection target 41 and the first tag particle 43 are bound via the first capture substance 42 (E and G), when the second detection target 51 and the second tag particle 53 are bound via the second capture substance 52 (F and H), the change in signal greatly differs from A to D. More specifically, when the bound particles of the first detection target 41 and the first tag particle 43 pass through the pore 22 in tandem (E), and when the bound particles of the second detection target 51 and the second tag particle 53 pass through the pore 22 in tandem (F), a detection signal having two continuous peaks is obtained as a bimodal pulse signal. When the bound particles of the first detection target 41 and the first tag particle 43 pass through the pore 22 side by side (G), and when the bound particles of the second detection target 51 and the second tag particle 53 pass through the pore 22 side by side (H), a pulse-like unimodal detection signal having a large change in signal is obtained. When the detection target and the tag particle pass through the pore obliquely side by side, an intermediate response signal between E and G or between F and H is obtained, as in the above-described embodiments.

When the first tag particle 43 and the second tag particle 53 are made to have different sizes, the case in which the bound particles of the first detection target 41 and the first tag particle 43 pass, and the case in which the bound particles of the second detection target 51 and the second tag particle 53 pass can be distinguished.

Hence, even when the single first detection target 41 and the single second detection target 51 have almost the same size, and no current signal difference can be observed between the single particles, it is possible to determine whether the current signal represents the bound state of the first detection target 41 and the first tag particle 43 or the bound state of the second detection target 51 and the second tag particle 53. This makes it possible to determine whether the detection target existing in the sample is the first detection target 41 or the second detection target 51, or includes both or neither.

The determination by the above-described arrangement is possible when the detection target and the tag particle have the same size. The size of the detection target is realistically 100 nm or more. The size is preferably 300 nm or more, and more preferably 500 nm or more. When the size of the first detection target 41 and that of the second detection target 51 are almost equal, the first tag particle 43 and the second tag particle 53 are made to have a size difference of 10% or more, thereby facilitating identification.

Note that in the above-described example, two types of detection targets are identified. Three or more types of detection targets can also be identified by increasing the number of types of tag particles based on the same concept.

As described above, according to this embodiment, the first tag particle 43 bound to the first capture substance 42 to be specifically bound to the first detection target 41 and the second tag particle 53 bound to the second capture substance 52 to be specifically bound to the detection target 51 are used as the reagent. Hence, the plurality of types of detection targets 41 and 51 that can exist in the sample can independently be detected. It is therefore possible to obtain the same effect as in the above-described first embodiment, as a matter of course, and also detect/identify, among viruses or bacteria having an equal size or shape, a plurality of types of viruses or bacteria that can exist in the sample at a high sensitivity using the specificity of the antigen-antibody reaction.

A simple case in which the capture substance is bound to the detection target only at one portion has been described above. However, the embodiment is not limited to this, and the same concept applies to a case in which the capture substance is bound to the detection target at a plurality of portions.

(Fourth Embodiment)

The arrangement of a biomolecule detection apparatus used in this embodiment is the same as in FIG. 1 described in the first embodiment.

In this embodiment, assume that two types of detection targets (biomolecules) can exist in a sample. Also assume that the particles are very small, and the current detection signal for a single particle is small.

If tag particles bound to a capture substance (antibody) to be specifically bound to the detection target are used as a reagent, and the current detection signal intensity for the single tag particle and that for the bound state of the detection target and the tag particle are compared, as in the third embodiment, it is difficult to obtain a clear difference in the current signal intensity because of the small size difference resulted from the small detection target.

Figure 9A:
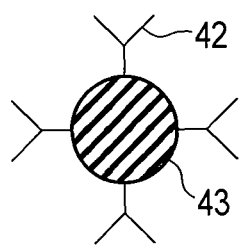
FIGS. 9A to 9F are views showing an example of a reagent used in the fourth embodiment.
Figure 9B:
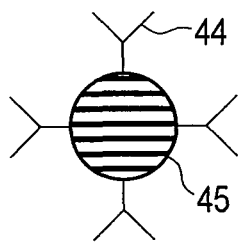
Figure 9E:
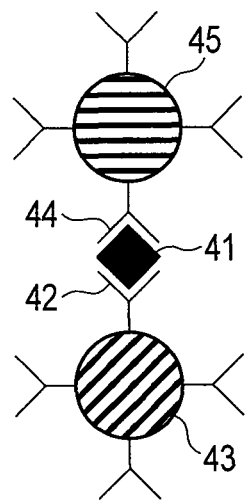
Figure 9C:
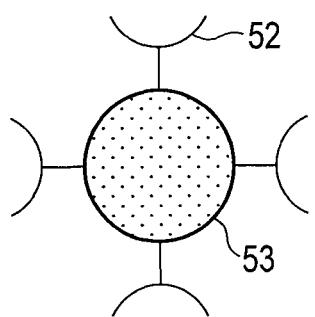
Figure 9D:
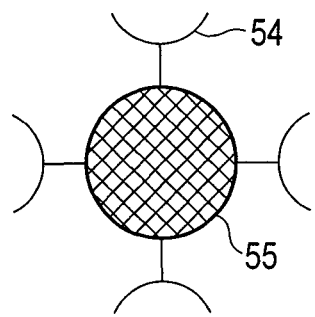

In this embodiment, two tag particles bound to the first detection target and two tag particles bound to the second detection target are used as a reagent, as shown in FIGS. 9A to 9F. FIG. 9A shows a first tag particle 43 bound to a first capture substance 42 to be specifically bound to the first portion of a first detection target 41. FIG. 9B shows a second tag particle 45 bound to a second capture substance 44 to be specifically bound to the second portion of the first detection target 41. FIG. 9C shows a third tag particle 53 bound to a third capture substance 52 to be specifically bound to the first portion of a second detection target 51. FIG. 9D shows a fourth tag particle 55 bound to a fourth capture substance 54 to be specifically bound to the second portion of the second detection target 51.

Figure 9F:
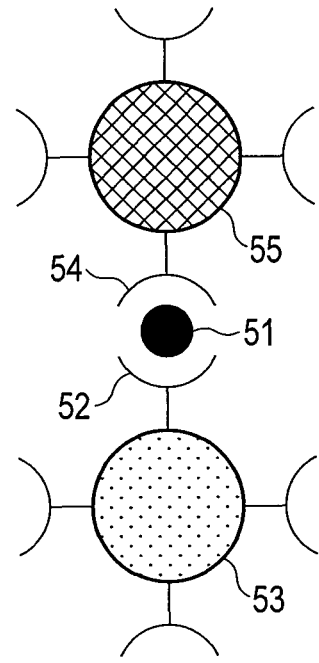

When this reagent is introduced into the sample, the tag particles 43 and 45 are bound to the detection target 41 via the capture substances 42 and 44, as shown in FIG. 9E. In addition, the tag particles 53 and 55 are bound to the detection target 51 via the capture substances 52 and 54, as shown in FIG. 9F. The first and second tag particles 43 and 45 and the third and fourth tag particles 53 and 55 are made to have different sizes.

Figure 10:
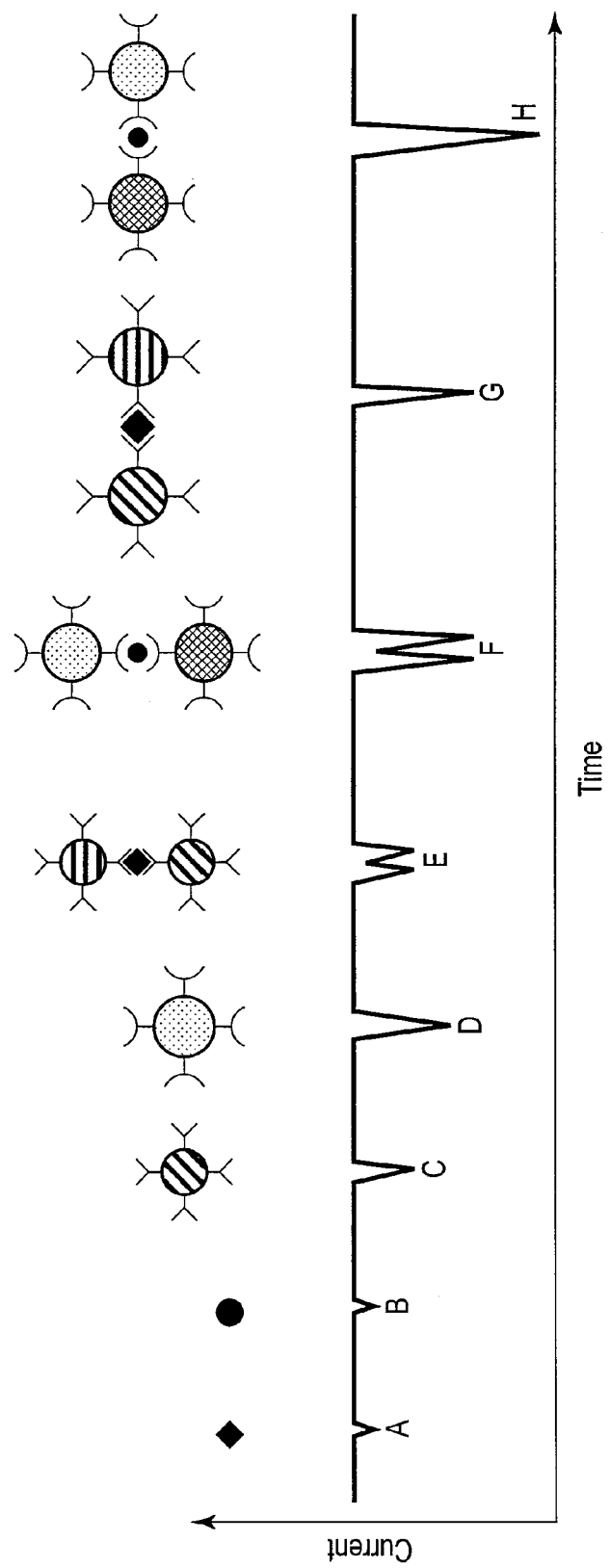
FIG. 10 is a timing chart showing a current signal detected in the fourth embodiment.

A first chamber 11 is filled with the sample and the above-described reagent, and test is performed as in the above-described embodiments. As in the first to third embodiments, the change in current depends on whether the particle includes the single detection target, the single tag particle, or the composite particle, as shown in FIG. 10.

In this embodiment, when the first detection target 41 exists in the sample, the first tag particle 43 and the second tag particle 45 are bound via the first detection target 41. When the second detection target 51 exists in the sample, the third tag particle 53 and the fourth tag particle 55 are bound via the second detection target 51. That is, when a current detection signal by the composite particle of the first tag particle 43 and the second tag particle 45 is observed, the existence of the first detection target 41 is revealed. When a current detection signal by the composite particle of the third tag particle 53 and the fourth tag particle 55 is observed, the existence of the second detection target 51 is revealed. Even the detection target that is very small as a single particle and difficult to identify can be identified by measuring signal by the tag particles.

That is, even when the size of the detection target is very small, it can sufficiently be detected by causing the tag particles to have observable sizes. The sizes of the tag particles are 100 nm or more, preferably 300 nm or more, and more preferably 500 nm or more. The sizes of the first tag particle 43 and the second tag particle 45 can be either equal or different. Similarly, the sizes of the third tag particle 53 and the fourth tag particle 55 can be either equal or different. The first and second tag particles 43 and 45 and the third and fourth tag particles 53 and 55 are set to be identifiable, and the tag particles to be identified are made to have a size difference of 10% or more, thereby facilitating identification.

Note that in the above-described example, two types of detection targets are identified. Three or more types of detection targets can also be identified by increasing the number of types of tag particles based on the same concept.

As described above, according to this embodiment, even when a plurality of types of detection targets that are very small as single particles and difficult to identify exist in the sample, they can be identified by measuring the signal by the tag particles. It is therefore possible to obtain the same effect as in the above-described first embodiment, as a matter of course, and also obtain the following advantage. That is, it is possible to detect/identify, among viruses or bacteria having an equal size or shape, a plurality of types of very small viruses or bacteria that can exist in the sample at a high sensitivity using the specificity of the antigen-antibody reaction.

(Fifth Embodiment)

In the first to fourth embodiments, a case in which one detection target is bound to one tag particle has been described. This often holds when only a small number of detection targets exist in the sample. In this case, the number of tag particles bound to the capture substance is much larger than the number of detection targets. A state in which a plurality of detection targets are bound to one tag particle is rarely observed, and one detection target is bound at most. Hence, in this case, the composite signal of the single detection target and the tag particle is obtained.

Assume that two types of tag particles respectively bound to the first and second portions of one detection target are used as a reagent. When the detection targets and the first tag particles are mixed, and the second tag particles are mixed after that, composite particles each formed by bonding one detection target, one first tag particle, and one second tag particle or particles that are not bound at all exist. In this case, the composite signal of the first tag particle, the single detection target, and the second tag particle is obtained.

Figure 11A:
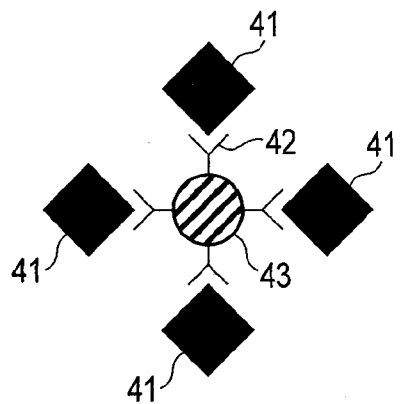
FIGS. 11A to 11D are views showing bound states obtained when there is an enormous number of targets to be detected in the first to fourth embodiments so as to explain the fifth embodiment.
Figure 11B:
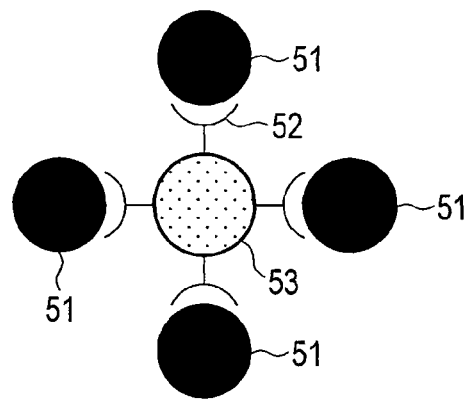

On the other hand, when a number of detection targets exist in the sample, a plurality of detection targets may be bound to one tag particle, as shown in FIGS. 11A and 11B. In this case, a composite particle larger than the tag particle size by the size of the plurality of bound detection targets is produced. When this composite particle passes through a pore 22, a larger change in current signal is measured.

Figure 11C:
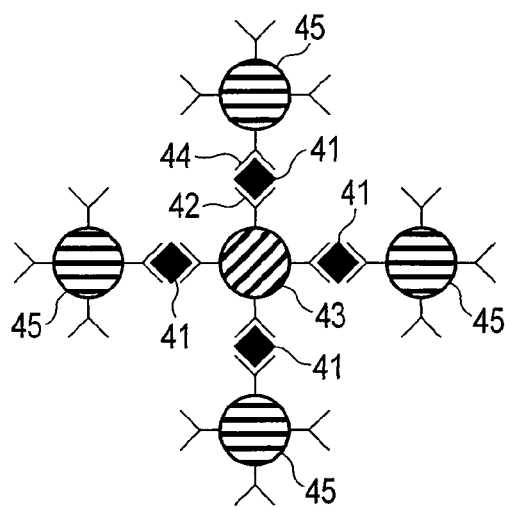
Figure 11D:
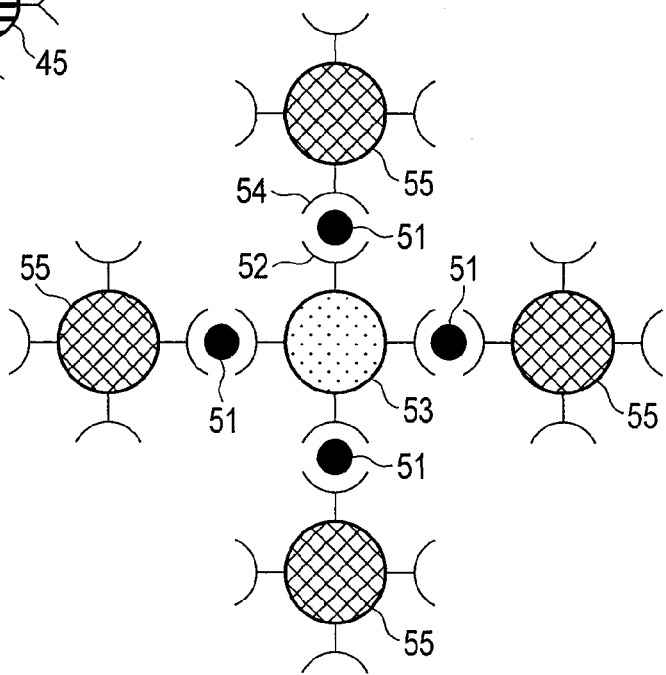

Assume that the first tag particle and the second tag particle bound to different portions of the detection target are used as a reagent. When the detection targets and the first tag particles are mixed, and the second tag particles are mixed after that, a plurality of detection targets are bound around the first tag particle, and the second tag particle is bound to each detection target, as shown in FIGS. 11C and 11D. In this case, a composite signal having the total size of the first tag particle, the plurality of detection targets, and the plurality of second tag particles is produced. When this composite particle passes through the pore 22, a larger change in current signal is measured.

Note that FIGS. 11A to 11D illustrate only the case in which the detection targets are bound to all capture substances of the tag particles. However, the embodiment is not limited to this. Even when the detection targets are bound to only some of the capture substances, they can be identified because the waveform or intensity is different from that of the signal of a single tag particle or the signal of a tag particle bound to anther detection target, as a matter of course.

In addition, when a plurality of detection targets exist, tag particles having different sizes are selected in correspondence with the respective detection targets, and therefore, the composite particles have different sizes. Since the obtained current signals also have different intensitys consequently, the type of each detection target can be identified.

Various embodiments have been described heretofore. At any rate, to identify the type of a detection target, it is only necessary to detect that the tag particle bound to the capture substance to be specifically bound to the detection target exists not as a single particle but as a composite particle.

(Sixth Embodiment)

In the fifth embodiment, a plurality of targets to be detected were described as being bound to one tag particle. Conversely, there may be a case where a plurality of tag particles are bound to one target to be detected when the number of tag particles is much larger than the number of target.

Figure 12A:
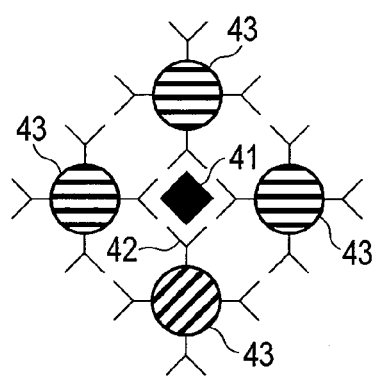
FIGS. 12A and 12B are views illustrating the sixth embodiment and showing a state in which a plurality of tag particles are bound to a single target to be detected.
Figure 12B:
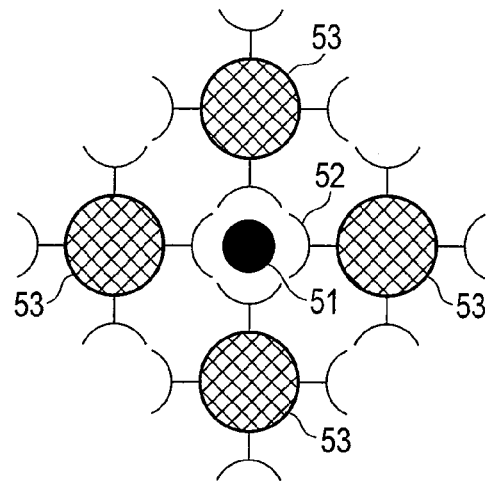

FIG. 12A illustrate a case where a plurality of tag particles 43 are bound to one target 41 to be detected, with capture substances 42 located therebetween. The target 41 has a number of portions to which capture substances 42 are to be bound. When the capture substances 41 are bound to those portions, a plurality of tag particles 43 are bound to one target 41 to be detected. Likewise, a plurality of tag particles 53 are bound to another target 51 to be detected, with the capture substances 52 located therebetween, as shown in FIG. 12B. When these complex particles have passed through the pore 22, apparent size of the complex particle is much larger than a single particle and then a bigger change is observed in the current signal.

The capture substances 42 and 52 to be bound to the targets 41 and 51 to be detected can have properties specific to them. Because of this, the targets 41 and 51 can be discriminated from each other by changing the features of tag particles 43 and 53, such as their sizes.

(Seventh Embodiment)

Figure 13:
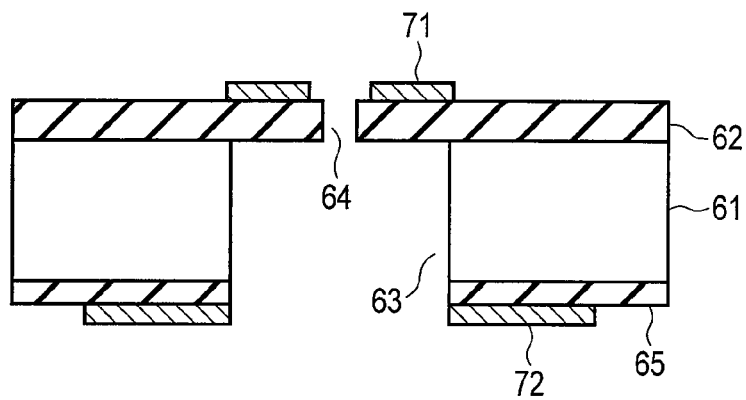
FIG. 13 is a sectional view showing the schematic arrangement of a detection unit used in a biomolecule detection apparatus according to the seventh embodiment.

FIG. 13 is a sectional view showing the sectional arrangement of a detection unit used in a biomolecule detection apparatus according to the seventh embodiment.

An insulating film 62 of $SiO_2$ or the like is provided on an Si substrate 61. A through-hole 63 is formed in the Si substrate 61. A pore 64 communicating with the through-hole 63 is formed in the insulating film 62. A disk-shaped first electrode 71 is formed on the insulating film 62 so as to be coaxial with the pore 64. An insulating film 65 is formed on the lower surface of the Si substrate 61. A disk-shaped second electrode 72 is formed on the insulating film so as to be coaxial with the through-hole 63.

Figure 14:
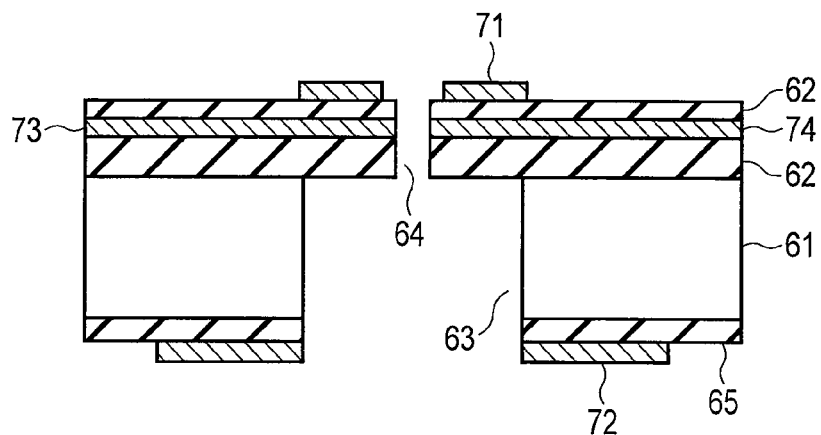
FIG. 14 is a sectional view showing a modification of the seventh embodiment.

The first electrode 71 and the second electrode 72 suffice as the electrodes. As shown in FIG. 14, a third electrode 73 and a fourth electrode 74 may additionally be buried in the insulating film 62 on the left and right sides of the pore 64 so as to face each other.

The arrangement shown in FIG. 13 can be formed by a normal semiconductor manufacturing process. For example, the $SiO_2$ insulating film 62 is formed on the upper surface of the Si substrate 61 by thermal oxidation, CVD, or the like. A conductive film prospectively serving as the first electrode 71 is formed on the insulating film 62. The $SiO_2$ insulating film 65 is formed on the lower surface. A conductive film prospectively serving as the second electrode 72 is formed on the insulating film 65. The conductive film on the upper surface side is processed into the first electrode pattern by pattern etching, and the pore 64 is formed in the insulating film 62. The conductive film on the lower surface side is processed into the second electrode pattern, and the through-hole 63 is formed in the Si substrate 61.

As for the arrangement shown in FIG. 14, for example, the $SiO_2$ insulating film 62 is formed on the upper surface of the Si substrate 61 by thermal oxidation, CVD, or the like. A conductive film prospectively serving as the third electrode 73 and fourth electrode 74 is formed on the insulating film 62. The conductive film at the opening portion of the pore 64 is etched into a stripe pattern having a width much smaller than the opening diameter of the pore 64. The $SiO_2$ insulating film 62 is additionally stacked by thermal oxidation, CVD, or the like. A conductive film prospectively serving as the first electrode 71 is formed on the insulating film 62. The $SiO_2$ insulating film 65 is formed on the lower surface. A conductive film prospectively serving as the second electrode 72 is formed on the insulating film 65. The conductive film on the upper surface side is processed into the first electrode pattern by pattern etching, and the pore 64 is formed in the insulating film 62 so as to divide the stripe pattern. The conductive film on the lower surface side is processed into the second electrode pattern, and the through-hole 63 is formed in the Si substrate 61.

A first chamber (cap vessel capable of being filled with a liquid) capable of being filled with an electrolyte solution and a reagent is added to the upper side of the detection unit having the above-described arrangement. A second chamber capable of being filled with the electrolyte solution is added to the lower side of the detection unit. A current flowing between the electrodes 71 and 72 is measured, thereby applying the arrangement to the first to fifth embodiments and detecting a target to be detected.

A fine particle passing through the pore 64 can also be detected by measuring a current flowing between the electrodes 73 and 74 by the example shown in FIG. 14. More specifically, the detection is done by observing a change in the impedance between the electrodes 73 and 74 when the target to be detected passes through the pore 64. As the change in the impedance, a change in the AC impedance, a change in the resistance (a change in the current or voltage), or the like is observed. When the pore 64 and the target to be detected have a gap of nm order between them, observation by a tunnel current is also possible. In the example shown in FIG. 14, since the distance between the electrodes 73 and 74 is short, the change in the current signal caused by the passage of the fine particle can be measured at a high sensitivity. This can further increase the fine particle detection accuracy.

As described above, according to this embodiment, the detection unit of the biomolecule detection apparatus can be formed only by using the semiconductor materials and the normal semiconductor process. It is therefore possible to inexpensively form a very small detection unit.

(Modifications)

Note that the present invention is not limited to the above-described embodiments.

The arrangement of the detection unit used in the embodiments is not limited to that in FIG. 1, 13, or 14. The arrangement need only have a pore between two chambers and be capable of performing energization by electrodes between the two chambers. The first and second electrodes need not always be fixed to the detection unit itself. The arrangement need only bring the first electrode into contact with the liquid in the first chamber and the second electrode into contact with the liquid in the second chamber at the time of use. Alternatively, the arrangement may use an open vessel, form a pore between the first region and the second region, arrange the first electrode in the first region, arrange the second electrode arranged in the second region, and apply electrical current between the first electrode and the second electrode.

As the tag particle, a bead other than the polystyrene bead may be used. A silica bead, a magnetic bead, or a metal fine particle can also be used. The tag particle preferably has a spherical shape for easy identification. However, the shape is not necessarily limited to this. As for the charged state of the tag particle, it need not always be charged negatively and may charged positively. However, when a reagent formed by mixing a plurality of types of tag particles is used, the tag particles are preferably uniformly charged negatively or positively. When a magnetic bead is used, the particle is moved by the magnetic field. Hence, the surface charge need not particularly be worried about. The detection current can either increase or decrease upon passage of a particle, and the change is set by the combination of the liquid to energize and the material of the particle to be detected.

When a plurality of types of tag particles are used, they need not always have different sizes, and may have different shapes, charging potentials, conductivities, electron affinities, or masses. The difference in the change in current upon passing through the pore can also be measured by these differences. In the embodiments, the current produced when the target to be detected passes through the pore is measured. However, not the change in current but a change in another signal such as voltage or AC impedance may be measured.

The detection target is not necessarily limited to a biomolecule such as a virus or a bacterium. Any other fine particle can be detected if it changes the current (ion current or tunnel current) flowing through the liquid upon passing.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A sample detection method comprising:
using a sample detection apparatus including an insulating partition configured to divide a first region and a second region, a pore formed in the partition and configured to make the first region and the second region communicate, a first electrode arranged in the first region, and a second electrode arranged in the second region;
introducing a reagent containing a capture substance to be specifically bound to a target to be detected and a tag particle bound to the capture substance into the first region together with a sample, and filling the second region with an electrolyte solution;
applying electrical current between the first electrode and the second electrode through the pore, and observing a change in a conductive state between the first electrode and the second electrode when the target and the tag particle to be detected in the first region passes through the pore; and
judging presence/absence of the target to be detected in the sample based on the measured change in the conductive state,
wherein:
the reagent contains a first capture substance to be specifically bound to a first portion of the target to be detected, a first tag particle bound to the first capture substance, a second capture substance to be specifically bound to a second portion of the target to be detected, and a second tag particle bound to the second capture substance, and
in the judging the presence/absence of the target to be detected, it is judged that the target to be detected exists in the sample when the change in the conductive state caused by passage of the first tag particle and the change in the conductive state caused by passage of the second tag particle are detected continuously or in a combinational manner.

2. The method according to claim 1, wherein the target to be detected includes a plurality of types of targets to be detected, and
the first and second capture substances and the first and second tag particles are different for each of the plurality of types of targets to be detected.

3. The method according to claim 1, wherein a size of each of the first tag particle and the second tag particle is larger than a size of the target to be detected.

4. The method according to claim 1, wherein the target to be detected is a particle.

5. The method according to claim 1, wherein the first and second capture substances are antibodies.

* * * * *